(12) United States Patent
Kim et al.

(10) Patent No.: US 6,719,684 B2
(45) Date of Patent: Apr. 13, 2004

(54) MICRO CAPSULE TYPE ROBOT

(75) Inventors: Byungkyu Kim, Seoul (KR); Younkoo Jeong, Seoul (KR); Taesong Kim, Seoul (KR); Jong-Oh Park, Seoul (KR); Siyoung Song, Gyeonggi-Do (KR)

(73) Assignee: Korea Institute of Science and Technology (KR)

( * ) Notice: Subject to any disclaimer, the term of this patent is extended or adjusted under 35 U.S.C. 154(b) by 0 days.

(21) Appl. No.: 10/131,563

(22) Filed: Apr. 23, 2002

(65) Prior Publication Data
US 2003/0092964 A1 May 15, 2003

(30) Foreign Application Priority Data

Nov. 12, 2001 (KR) ........................................ 2001-70191

(51) Int. Cl.[7] .................................................. A61B 1/00
(52) U.S. Cl. ....................... 600/101; 600/109; 600/118; 600/160
(58) Field of Search ................................. 600/101, 109, 600/118, 160, 179, 476; 348/65, 68, 74–76

(56) References Cited

U.S. PATENT DOCUMENTS

| | | | | |
|---|---|---|---|---|
| 5,662,587 A | * | 9/1997 | Grundfest et al. | 600/114 |
| 5,984,860 A | * | 11/1999 | Shan | 600/116 |
| 6,162,171 A | * | 12/2000 | Ng et al. | 600/114 |
| 6,240,312 B1 | * | 5/2001 | Alfano et al. | 600/476 |
| 6,402,686 B1 | * | 6/2002 | Ouchi | 600/139 |
| 2002/0042562 A1 | * | 4/2002 | Meron et al. | 600/361 |

FOREIGN PATENT DOCUMENTS

| | | | |
|---|---|---|---|
| GB | PCT/GB97/02523 | * | 3/1998 |
| JP | 407289504 A | * | 11/1995 |

* cited by examiner

Primary Examiner—John P. Leubecker
(74) Attorney, Agent, or Firm—Ostrolenk, Faber, Gerb & Soffen, LLP

(57) ABSTRACT

In a micro capsule type robot for examining the internal organs of a human body, by installing stopping unit for stopping or delaying moving of a micro capsule type robot at a certain examination position of the internal organs according to a stop control signal inputted from outside of a human body, the micro capsule type robot can be fixed to a certain position of the internal organs of a human body or its movement can be delayed in case of need in spite of peristalsis of the internal organs in order to examine the certain position minutely, accordingly a lesion judgement rate can be improved and a diagnosis function of the micro capsule type robot can be heightened.

12 Claims, 6 Drawing Sheets

MICRO CAPSULE TYPE ROBOT

BACKGROUND OF THE INVENTION

1. Field of the Invention

The present invention relates to a micro capsule type robot, and in particular to a micro capsule type robot which is capable of stopping or delaying at a certain portion of the internal organs of a human body in accordance with a stop control signal inputted from outside of the human body.

2. Description of the Prior Art

An endoscope is used for examining or treating a disease of the internal organs without performing surgeries. However, because the large intestine is curved at a steep angle, in performing of an endoscopy in the large intestine a patient may feel much pain, accordingly it has not been welcomed by patients In more detail, because the large intestine is curved steeply, in the large intestine endoscopy patient's pain and a lesion judgement are largely influenced by experience and skill of a doctor.

Recently, in order to solve the above-mentioned problem of an endoscopy in the large intestine, a virtual colonoscopy or a gene examination method, etc. have been developed. However, a doctor can not directly measure an affected part or perform a biopsy, etc. by the methods, they are regarded as indirect methods. In addition, by developing a swallowable micro capsule type endoscope for transmitting certain image information of the internal organs to outside, the small intestine which can not be examined by the conventional endoscope can be examined, accordingly a range of a medical examination has been broadened.

In the above-mentioned micro capsule type endoscope, the small intestine can be examined by transmitting information received from a camera unit of the micro capsule type endoscope to outside of a human body through a wireless transmission module.

However, because moving of the micro capsule type endoscope including the wireless camera unit only depends on natural peristalsis of the internal organs, it is impossible to stop the micro capsule type endoscope at a certain position of the internal organs even a doctor wants to examine a specific portion.

It means the micro capsule type endoscope for examining the internal organs has an image information transmission function, but it has not a stop function.

SUMMARY OF THE INVENTION

Accordingly, in order to solve the above-mentioned problems, it is an object of the present invention to provide a micro capsule type robot which is capable of stopping or delaying its movement at a certain examination position according to a stop signal inputted from outside.

In order to achieve the above-mentioned object, in a micro capsule type robot having a camera for examining the internal organs of a human body, a micro capsule type robot includes stopping means installed to a body of a micro capsule type robot for stopping or delaying moving of the micro capsule type robot at a certain examination position according to a stop signal inputted from outside of a human body.

In addition, a micro capsule type robot includes a capsule type robot body, a camera unit installed to the capsule type robot body in order to observe the internal organs of a human body, a lighting unit installed to the capsule type robot body and throwing a light on the internal organs so as to capture images inside the internal organs by the camera unit, a transmitter-receiver installed to the capsule type robot body, transmitting image information of the camera unit to the outside and receiving a control signal inputted from outside of a human body, stopping means installed to the capsule type robot body for stopping or delaying the capsule type robot body at a certain position of the internal organs, a control unit installed to the capsule type robot body and controlling operation of the camera unit, the lighting unit, the transmitter-receiver and the stopping means, and a power supply unit installed to the body and supplying power to the camera unit, the lighting unit, the transmitter-receiver, the stopping means and the control unit.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE PREFERRED EMBODIMENT

Embodiments of the present invention will be described with reference to accompanying drawings.

Figure 1A:
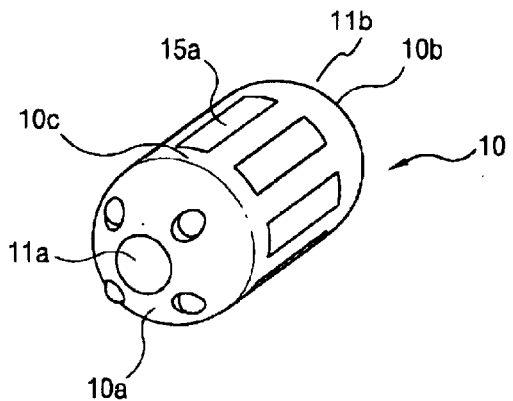
FIG. 1A is a perspective view illustrating a first embodiment of a micro capsule type robot in accordance with the present invention before operating a stopping means.
Figure 1B:
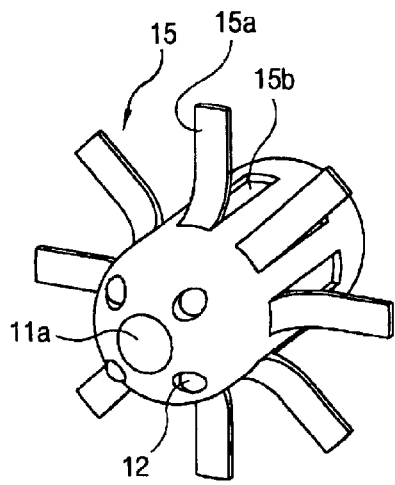
FIG. 1B is a perspective view illustrating the operation of a stopping means of the micro capsule type robot of FIG. 1A.
Figure 1C:
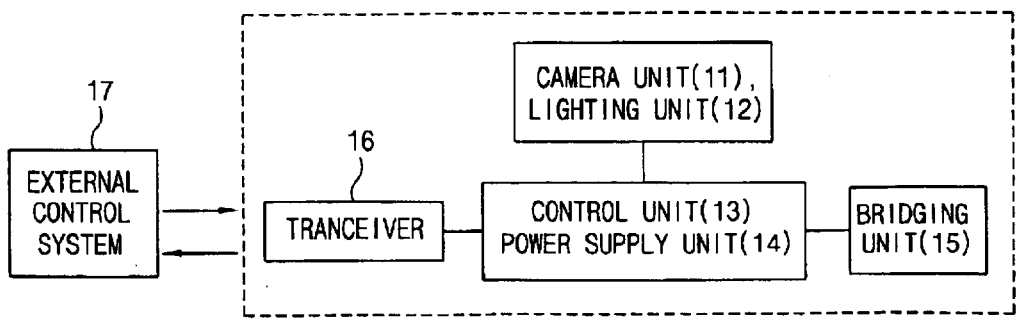
FIG. 1C is a block diagram illustrating a construction of the micro capsule type robot of FIG. 1A.

FIG. 1A is a perspective view illustrating a first embodiment of a micro capsule type robot in accordance with the present invention before operating a stopping means, FIG. 1B is a perspective view illustrating the operation of the stopping means of the micro capsule type robot of FIG. 1A, and FIG. 1C is a block diagram illustrating a construction of the micro capsule type robot of FIG. 1A.

As depicted in FIGS. 1A, 1B and 1C, a micro capsule type robot in accordance with a first embodiment of the present invention includes a body 10, a camera unit 11 installed to the body 10 for examining the internal organs of a human body, a lighting unit 12 installed to the body 10 for throwing a light on the internal organs of a human body, a transmitter-receiver 16 installed to the body 10, for transmitting image information received from the camera unit 11 to the outside and receiving a control signal inputted from outside, a stopping means installed to the body 10 for stopping or delaying the body 10 at a certain position of internal organs, a control unit 13 installed to the body 10 and controlling the operation of the camera unit 11, the lighting unit 12, transmitter-receiver 16 and the stopping means, and a power supply unit 14 installed to the body 10 and supplying power to the camera unit 11, the lighting unit 12, the transmitter-receiver 16, the stopping means and the control unit 13.

The body 10 is constructed with a hemispheric front unit 10a, a hemispheric rear unit 10b and a cylinder unit 10c. The body 10 has a capsule shape in whole and its size is suitable for swallow. Herein, a size of the body 10 is about 13 mm. And, the body 10 is made of materials having a biocompatibility.

The camera unit 11 includes an external lens 11a and a camera element (CCD or CMOS) directly connected to the lens 11a and is installed to the front unit 10a of the body 10. The camera unit 11 can also be installed to the rear unit 10b, as indicated by numeral 11b. It is preferable for the camera unit 11 to have a function for zooming in or out on the internal organs, or changing the imaging direction.

In the meantime, the lighting unit 12 is a light source system providing a light required for capturing images of the internal organs, a white LED (light emitting diode) is installed to the front unit 10a of the body 10 with the camera unit 11. The number and the direction of the white LEDs can be adjusted by a required illumination.

As depicted in FIGS. 1A and 1B, in the first embodiment of the present invention, the stopping means stops or delays moving of the body 10 by projecting bridging members 15a of a bridging unit 15 from the body 10 and hanging on the internal wall of the internal organs in accordance with a stop signal.

A plurality of grooves 15b are radially placed on the cylinder unit 10c of the body 10 in a length direction, the bridging unit 15 includes a plurality of bar-shaped bridging members 15a one end is respectively fixed to each of the plurality of grooves 15b, when the micro capsule type robot moves, each bridging member 15a is placed inside each groove 15b, when the moving of the robot is stopped or delayed, the bridging members 15a are projected from the body 10 according to a stop signal.

In the first embodiment of the present invention, the bridging members 15a are actuator made of EAP (electroactive polymer) such as IPMC (ionic polymer metal composite), or EP(Electrostrictive polymer).

In addition, when the micro capsule type robot body 10 is put into the internal organs of a human body, in order to prevent a rejection symptoms of a human body, the body 10 is made of polymer having a biocompatibility such as urethane, etc., and by forming the bridging unit 15 on the body 10 as one body, a structure of the robot can be simplified.

And, the external control system 17 processes image information of the internal organs and transmits a control signal to the micro capsule type robot. For that, the external control system 17 has two-way transmission and reception functions and includes command generation unit for controlling the robot. In addition, a wireless transmission frequency and a wireless reception frequency have not to affect affiliates and have to be harmless for the human body.

In the meantime, the operation of the micro capsule type robot having the above-mentioned construction will be described.

For an endoscopy, the micro capsule type robot is put into the internal organs of the human body and moves gradually inside the internal organs according to peristalsis of the internal organs.

Figure 5:
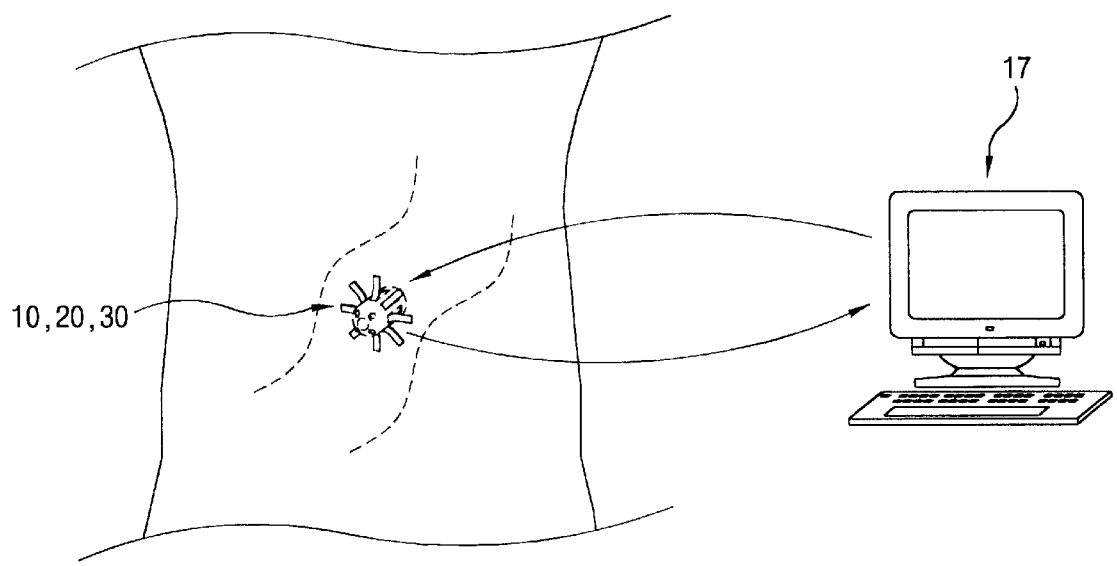
FIG. 5 is a schematic view illustrating a image information transmission and a stopping control when a micro capsule type robot in accordance with the present invention is put into the internal organs of a human body.

FIG. 5 is a schematic view illustrating an image information transmission and a stopping control when a micro capsule type robot in accordance with the present invention is put into the internal organs of a human body.

Each bridging member 15a as functional polymer is placed inside the each groove 15b in the moving of the robot. In more detail, when the micro capsule type robot moves, each bridging member 15a is uniformly arranged on the surface of the cylinder unit 10c.

In the meantime, as depicted in FIGS. 1C and 5, image information of the internal organs photographed by the camera unit 11 is wirelessly transmitted to the external control system 17, when the micro capsule type robot reaches a certain examination portion, a user wirelessly transmits a stop control signal to the transmitter-receiver 16 through the external control system 17 while observing the image on a monitor. The transmitter-receiver 16 receiving the control signal transmits the signal to the control unit 13, and the control unit 13 applies a voltage to the bridging members 15a as an actuator.

As depicted in FIG. 1B, when the voltage is applied to the bridging member 15a (actuator), the bridging member 15a is unfolded in the circumferential direction of the cylinder unit 10c of the body 10, it interferes the moving of the micro capsule type robot, accordingly the moving of the micro capsule type robot is stopped or delayed at the certain position in the internal organs. Herein, because functional polymer actuator uses a small quantity of power in operation and the micro capsule type robot has to stop repeatedly in operation, it is preferable to use functional polymer actuator as the bridging member 15a of the bridging unit 15. In the meantime, the camera unit 11 of the stopped robot can minutely photograph the certain portions of the internal organs.

Figure 2A:
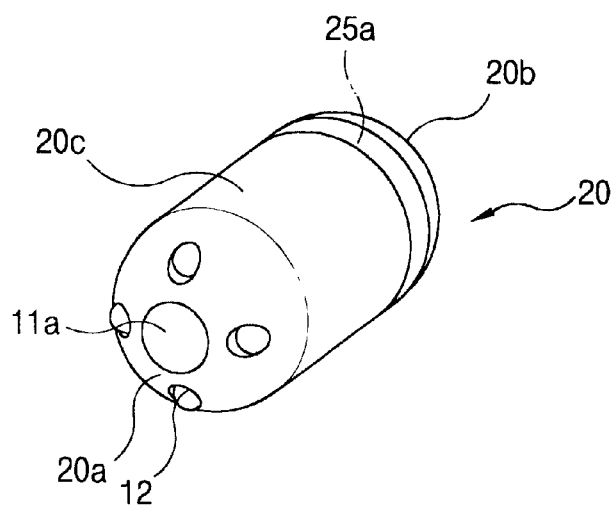
FIG. 2A is a perspective view illustrating a second embodiment of a micro capsule type robot in accordance with the present invention.
Figure 2B:
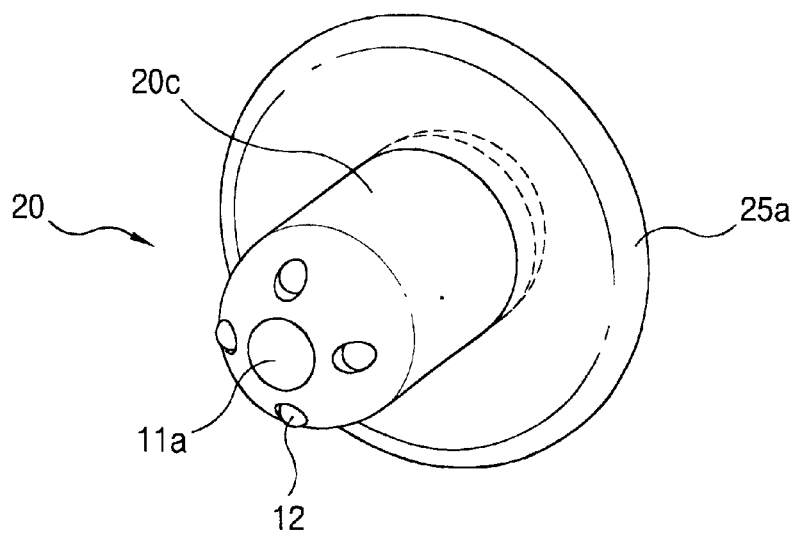
FIG. 2B is a perspective view illustrating the operation of a stopping means of the micro capsule type robot of FIG. 2A.

FIG. 2A is a perspective view illustrating the second embodiment of a micro capsule type robot in accordance with the present invention, and FIG. 2B is a perspective view illustrating the operation of the stopping means of the micro capsule type robot of FIG. 2A.

Figure 3A:
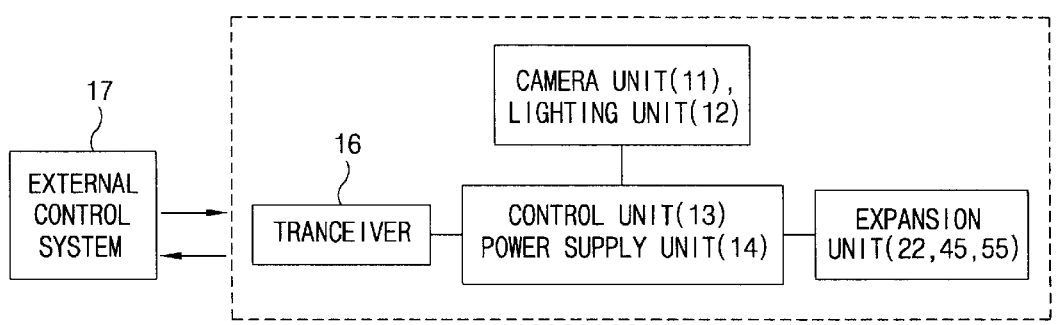
FIG. 3A is a block diagram illustrating a construction of the micro capsule type robot in accordance with the second embodiment of the present invention.
Figure 3B:
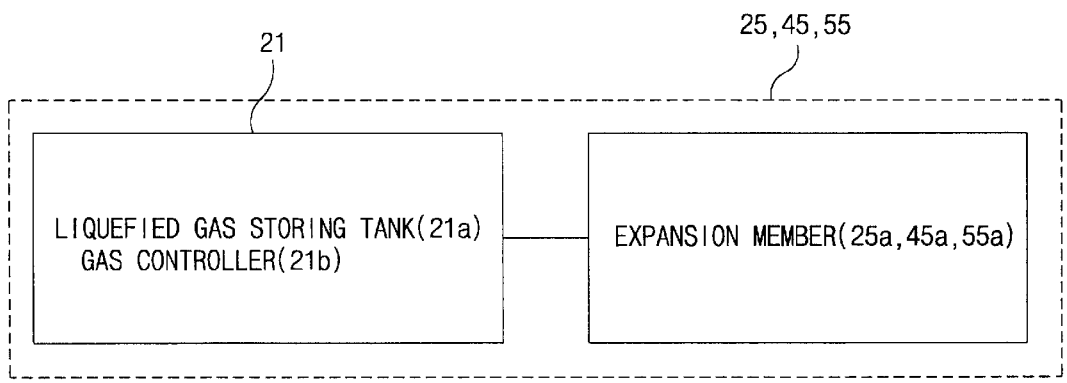
FIG. 3B is a block diagram illustrating a construction of an expansion unit of FIG. 3A.

In addition, FIG. 3A is a block diagram illustrating a construction of the micro capsule type robot in accordance with the second embodiment of the present invention, and FIG. 3B is a block diagram illustrating a construction of an expansion unit of FIG. 3A.

As depicted in FIGS. 2A, 2B, 3A and 3B, differentiating from the stopping means of the micro capsule type robot in accordance with the first embodiment of the present invention, in stopping means of the micro capsule type robot in accordance with the second embodiment of the present invention, moving of a body 20 is stopped or delayed by expanding an expansion unit 25 installed to the exterior of the body 20 in accordance with a control signal.

The expansion unit 25 is expanded by a gas supply from a gas supply unit 21 arranged inside the body 20, and the expansion unit 25 includes an expansion member 25a contracted by discharging gas when the robot moves. The gas supply unit 21 supplies gas by evaporating liquefied gas. It is preferable to use a member having an elastic force as the expansion member 25a in order to perform expansion and contraction smoothly according to a gas supply and a gas discharge In addition, the gas supply unit 21 is constructed with a liquefied gas storing tank 21a and a gas controller 21b.

As depicted in FIGS. 2A and 2B, the body 20 is constructed with a hemispheric front unit 20a, a hemispheric rear unit 20b and a cylinder unit 20c, and the expansion unit 25 is formed at the end of the cylinder unit 20c abutting on the rear unit 20b.

Figure 2C:
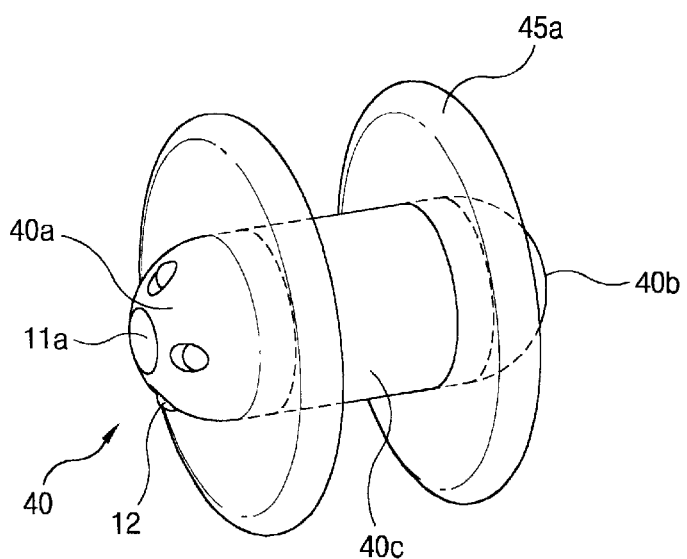
FIG. 2C is a perspective view illustrating a modification of the stopping means of the micro capsule type robot in accordance with the second embodiment of the present invention.
Figure 2D:
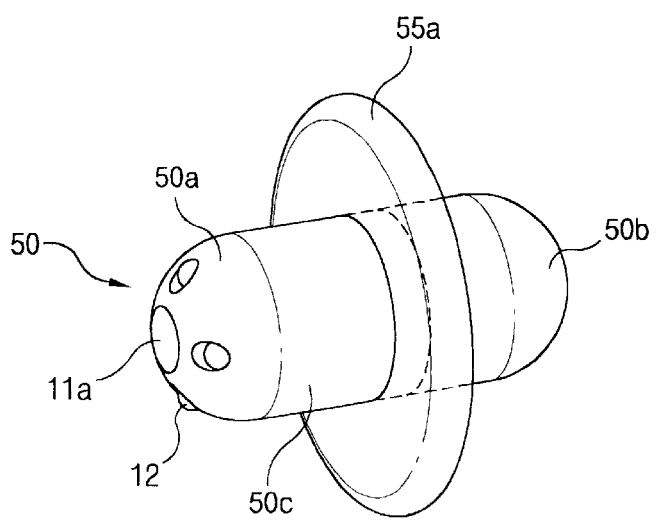
FIG. 2D is a perspective view illustrating a modification of the stopping means of the micro capsule type robot in accordance with the second embodiment of the present invention.

FIG. 2C is a perspective view illustrating a modification of the stopping means of the micro capsule type robot in accordance with the second embodiment of the present invention, and FIG. 2D is a perspective view illustrating a modification of the stopping means of the micro capsule type robot in accordance with the second embodiment of the present invention;

In the meantime, as depicted in FIGS. 2C and 2D, the expansion member 25a of the expansion unit 25 can be arranged on other portions of the body. In the meantime, as a modification of the expansion unit 25, an expansion member 45a of an expansion unit 45 is formed at the end of a cylinder unit 40c abutting on a rear unit 40b or an expansion member 55a of an expansion unit 55 is formed at the central portion of a cylinder unit 50c or the expansion member 55a of the expansion unit 55 is formed on the both ends of the cylinder unit 50c abutting on a rear unit 50b and a front unit 50a.

The operation of the micro capsule type robot in accordance with the second embodiment of the present invention will be described.

By the stopping means, for an endoscopy, the micro capsule type robot is put into the internal organs of a human body and moves gradually the internal organs of the human body.

As depicted in FIG. 2A, in moving, because gas is not supplied to the expansion member 25a, 45a, 55a of the expansion unit 25, 45, 55, the stopping means of the micro capsule type robot is in a contraction state according to a shape of the body 20, 40, 50 by the elastic force of the expansion member 25a, 45a, 55a. In the meantime, the expansion member 25a, 45a, 55a and the body 20, 40, 50 are made of materials having a biocompatibility in order to reduce rejection symptoms.

In the meantime, as depicted in FIGS. 3A, 3B and 5, captured images of the internal organs taken by the camera unit 11 is wirelessly transmitted to the external control system 17 through the transmitter-receiver 16. This occurs when the micro capsule type robot reaches a certain examination portion, the user wirelessly transmits a stop control signal to the transmitter-receiver 16 through the external control system 17 while observing the image on a monitor.

The transmitter-receiver 16 receiving the stop control signal transmits the signal to the control unit 13, and the control unit 13 operates the gas supply unit 21. Part of liquefied gas in the liquefied gas storing tank 21a of the gas supply unit 21 is evaporated by the gas controller 21b and is supplied to the expansion member 25a, 45a, 55a of the expansion unit 25, 45, 55, accordingly the expansion member 25a, 45a, 55a is expanded. In more detail, by the expansion of the expansion member 25a, 45a, 55a, the moving of the robot can be stopped or delayed on a certain portion of the internal organs. The camera unit 11 of the body 20, 40, 50 of the robot can photograph a certain portion of the internal organs minutely.

In the meantime, by discharging gas inside the expansion member by using the gas controller 21b, the micro capsule type robot can move again. Particularly, when a member having an elastic force is used for the expansion member, gas can be discharged more efficiently.

Figure 4A:
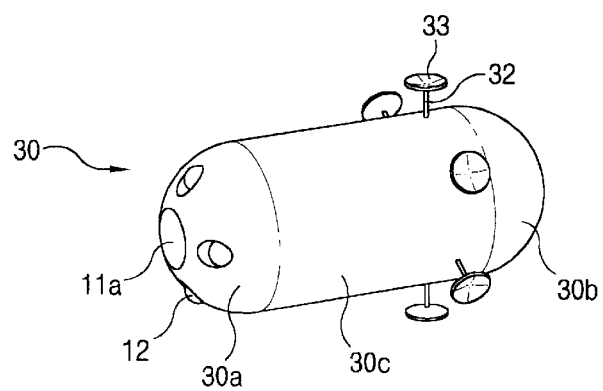
FIG. 4A is a perspective view illustrating the third embodiment of a micro capsule type robot in accordance with the present invention.
Figure 4B:
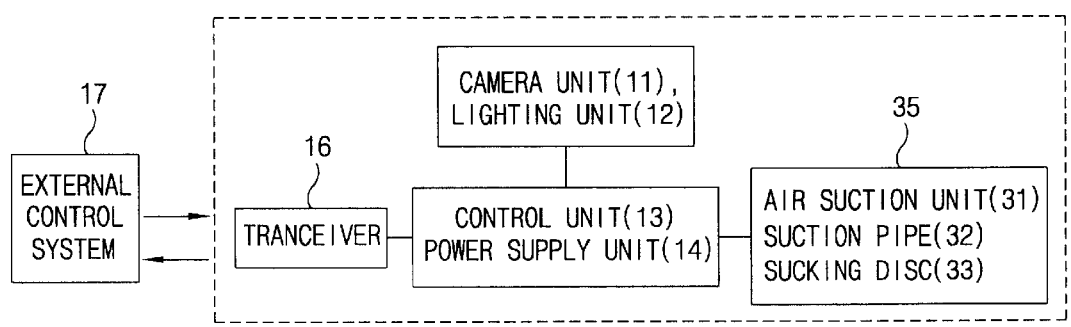
FIG. 4B is a block diagram illustrating a construction of the micro capsule type robot of FIG. 4A.

FIG. 4A is a perspective view illustrating a third embodiment of a micro capsule type robot in accordance with the present invention, and FIG. 4B is a block diagram illustrating a construction of the micro capsule type robot of FIG. 4A.

Stopping means of the micro capsule type robot in accordance with the third embodiment of the present invention includes a clinging unit 35 for stopping or delaying moving of the body by clinging to the internal wall of the internal organs in accordance with a control signal.

The clinging unit 35 includes an air suction unit 31 arranged inside the body and a suction pipe 32 one end is installed to the exterior of the body and the other end is a sucking disc 33. The suction pipe 32 sucks air by being connected to the air suction unit 31, and the sucking disc 33 clings to the internal organs, accordingly moving of the body is stopped or delayed.

Particularly, as depicted in FIGS. 4A and 4B, there are a plurality of suction pipes 32. The plurality of suction pipes 32 are radially arranged on the exterior of the body. When the moving of the body is stopped or delayed by clinging to a certain position of the internal organs by one of the plurality of suction pipes 32, connections between other suction pipes and the air suction unit 31 are cut off. A micro pump, or any pumping device can be used as the air suction unit 31.

The operation of the micro capsule type robot in accordance with the third embodiment of the present invention will be described.

By the above-mentioned stopping means, for an endoscopy, the micro capsule type robot is put into the internal organs of the human body and moves along the internal organs of the human body in accordance with peristalsis of the internal organs. Herein, the air suction unit 31 of the clinging unit 35 is not operated.

In the meantime, as depicted in FIGS. 4B and 5, image captured by the camera unit 11 is transmitted to the external control unit 17 by the transmitter-receiver 16, when the micro capsule type robot reaches a certain examination portion, a user transmits a stop control signal to the transmitter-receiver 16 through the external control unit 17 while observing the images on a monitor.

The transmitter-receiver 16 receiving the stop control signal transmits the signal to the control unit 13, and the control unit 13 operates the air suction unit 31. The micro pump as the air suction unit 31 generates a low pressure not greater than an air pressure, the low pressure generated by the micro pump is transmitted to the sucking disc 33 of the suction pipe 32, the sucking disc 33 clings to the internal organs, accordingly the moving of the robot is stopped or delayed.

Particularly, when one of the plurality of sucking discs clings to a certain position of the internal organs, the control unit 13 cuts off other suction pipes 32 having sucking discs 33 from the air suction unit 31 in order to prevent a pressure loss and set other suction pipes 32 free in the radial direction, accordingly the micro capsule type robot can be efficiently stopped at a certain position of the internal organs without damaging the internal organs.

Differentiating from the stopping means of the first embodiment or the second embodiment, in the stopping means in accordance with the third embodiment of the present invention, when a size of the micro capsule type robot is excessively smaller than a diameter of the internal organs, by clinging to a certain position of the internal organs by the clinging unit, the moving of the micro capsule type robot can be stopped or delayed more efficiently.

As described above, in a micro capsule type robot having a camera in order to examine the internal organs of a human body, the micro capsule type robot further includes a stopping means in order to stop or delay the moving of the micro capsule type robot on a certain examination portion of the internal organs according to a stop control signal inputted from outside and an external control unit processing the image information received through a transmitter-receiver and controlling the micro capsule type robot, accordingly it is possible to construct an endoscopy system using a micro capsule type robot.

In the micro capsule type robot in accordance with the present invention, moving of the micro capsule type robot can be stopped or delayed on a certain examination portion of the internal organs according to a stop control signal inputted from outside, in case of need, by fixing the robot to a certain position of the internal organs, the certain position can be minutely examined in spite of peristalsis of the internal organs, accordingly a lesion judgement rate can be improved and an examination efficiency of a micro capsule robot can be heightened.

As the present invention may be embodied in several forms without departing from the spirit or essential characteristics thereof, it should also be understood that the above-described embodiments are not limited by any of the details of the foregoing description, unless otherwise specified, but rather should be construed broadly within its spirit and scope as defined in the appended claims, and therefore all changes and modifications that fall within the metes and bounds of the claims, or equivalence of such metes and bounds are therefore intended to be embraced by the appended claims.

What is claimed is:

1. A micro capsule type robot having a camera for examining the internal organs of a human body, the micro capsule type robot, comprising:
    a stopping means installed to a body thereof for stopping or delaying moving of the micro capsule type robot at a certain examination position according to a stop control signal inputted from outside of a human body, wherein the stopping means stops or delays moving of the body by hanging on the internal wall of the internal organs by projecting a bridging member of a bridging unit from the body according to the stop control signal, and
    wherein the body is constructed with a front unit, a rear unit and a cylinder unit, a plurality of grooves are radially formed on the cylinder unit of the body in a length direction, and the bridging unit includes a plurality of bar-shaped bridging members respectively fixed to the plurality of grooves,
    wherein when the micro capsule type robot is moved, the bridging unit is placed inside the groove, when moving of the robot is stopped or delayed, the bridging member is projected from the groove in accordance with the stop control signal.

2. The micro capsule type robot of claim 1, wherein the bridging unit is an actuator made of functional polymer actuator of IPMC (ionic polymer metal composite).

3. The micro capsule type robot of claim 1, wherein the bridging unit is constructed as one body with the body.

4. The micro capsule type robot of claim 1, wherein the body is made of polymer having a biocompatibility.

5. The micro capsule type robot of claim 1, wherein the camera unit is installed to the front surface and the rear surface of the body.

6. A micro capsule type robot having a camera for examining the internal organs of a human body, the micro capsule type robot, comprising:
    a stopping means installed to a body thereof for stopping or delaying moving of the micro capsule type robot at a certain examination position according to a stop control signal inputted from outside of a human body wherein the stopping means stops or delays moving of the body by expanding an expansion unit installed to the exterior of the body in accordance with the control signal, and
    wherein the expansion unit is expanded by gas supply of a gas supply unit and includes an expansion member contracted by discharging gas when the robot is moved, and
    wherein the gas supply unit supplies gas by evaporating liquefied gas.

7. A micro capsule type robot having a camera for examining the internal organs of a human body, the micro capsule type robot, comprising:
    a stopping means installed to a body thereof for stopping or delaying moving of the micro capsule type robot at a certain examination position according to a stop control signal inputted from outside of a human body, wherein the stopping means stops or delays moving of the body by expanding an expansion unit installed to the exterior of the body in accordance with the control signal, and
    wherein the body is constructed with a hemispheric front unit, a hemispheric rear unit and a cylinder unit, and the expansion unit is formed at the end of the cylinder unit abutting on the rear unit.

8. A micro capsule type robot having a camera for examining the internal organs of a human body, the micro capsule type robot, comprising:
    a stopping means installed to a body thereof for stopping or delaying moving of the micro capsule type robot at a certain examination position according to a stop control signal inputted from outside of a human body, wherein the stopping means stops or delays moving of the body by expanding an expansion unit installed to the exterior of the body in accordance with the control signal, and
    wherein the body is constructed with a hemispheric front unit, a hemispheric rear unit and a cylinder unit, and the expansion unit is formed at the central portion of the cylinder unit.

9. A micro capsule type robot having a camera for examining the internal organs of a human body, the micro capsule type robot, comprising:
    a stopping means installed to a body thereof for stopping or delaying moving of the micro capsule type robot at a certain examination position according to a stop control signal inputted from outside of a human body, wherein the stopping means stops or delays moving of the body by expanding an expansion unit installed to the exterior of the body in accordance with the control signal, and wherein the body is constructed with a hemispheric front unit, a hemispheric rear unit and a cylinder unit, and the expansion unit is formed at both ends of the cylinder unit abutting on the front portion and the rear portion.

10. A micro capsule type robot having a camera for examining the internal organs of a human body, the micro capsule type robot, comprising:

a stopping means installed to a body thereof for stopping or delaying moving of the micro capsule type robot at a certain examination position according to a stop control signal inputted from outside of a human body, wherein the stopping means stops or delays moving of the body by clinging to the internal wall of the internal organs by a clinging unit installed to the exterior of the body in accordance with the control signal, and wherein the clinging unit includes a air suction unit arranged inside the body and a suction pipe having one end that is installed to the exterior of the body and another end that is a sucking disc, the suction pipe sucks air by being connected to the air suction unit, and the sucking disc clings to the inter wall of the internal organs, accordingly moving of the body is stopped or delayed.

11. The micro capsule type robot of claim 10, wherein a plurality of suction pipes are radially placed on the exterior of the body, when moving of the body is stopped or delayed by clinging to the internal wall of the internal organs by one of the plurality of suction pipes, connections between other suction pipes and the air suction unit are cut off.

12. The micro capsule type robot of claim 10, wherein the air suction unit is a micro pump.

* * * * *